United States Patent
Benitez Porras et al.

(10) Patent No.: US 10,793,849 B2
(45) Date of Patent: Oct. 6, 2020

(54) NUCLEIC ACID PURIFICATION CARTRIDGE

(71) Applicant: STAT-Diagnostica & Innovation, S.L., Barcelona (ES)

(72) Inventors: Francesc Benitez Porras, Valldoreix (ES); Josep Pareja Gómez, Sant Gregori (ES)

(73) Assignee: STAT-DIAGNOSTICA & INNOVATION S.L., Barcelona (ES)

( * ) Notice: Subject to any disclaimer, the term of this patent is extended or adjusted under 35 U.S.C. 154(b) by 0 days.

(21) Appl. No.: 15/508,752

(22) PCT Filed: Sep. 2, 2015

(86) PCT No.: PCT/EP2015/070045
§ 371 (c)(1),
(2) Date: Mar. 3, 2017

(87) PCT Pub. No.: WO2016/034620
PCT Pub. Date: Mar. 10, 2016

(65) Prior Publication Data
US 2017/0283792 A1    Oct. 5, 2017

(30) Foreign Application Priority Data
Sep. 3, 2014  (EP) .................................. 14183411

(51) Int. Cl.
*C12N 15/09*  (2006.01)
*B01L 3/00*   (2006.01)
*C12N 15/10*  (2006.01)

(52) U.S. Cl.
CPC ...... *C12N 15/1017* (2013.01); *B01L 3/50273* (2013.01); *B01L 3/502715* (2013.01);
(Continued)

(58) Field of Classification Search
CPC ........... C12N 15/1017; C12N 15/1003; C12N 15/10; C12N 15/09; B01L 3/502715; B01L 3/5027; B01L 3/502; B01L 3/50
(Continued)

(56) References Cited

U.S. PATENT DOCUMENTS 4,617,102 A     10/1986  Tomblin et al.
5,306,420 A  *   4/1994  Bisconte ................ B01D 61/18
                                                       210/143
(Continued)

FOREIGN PATENT DOCUMENTS

EP    1 300 680    * 11/1995  ............. G01N 33/49
EP    1 300 680 A2    4/2003

OTHER PUBLICATIONS

International Search Report and Written Opinion directed to related International Patent Application No. PCT/EP2015/070045, dated Nov. 26, 2015; 10 pages.
(Continued)

*Primary Examiner* — Christine T Mui
(74) *Attorney, Agent, or Firm* — Sterne, Kessler, Goldstein & Fox P.L.L.C.

(57) ABSTRACT

A microfluidic device is disclosed having an enclosed chamber containing a filter for purifying biological or chemical analytes from a complex biological sample, said chamber housing a plurality of ports in addition to said filter, as follows: a first port enabling gas communication of the chamber with a vacuum generator, via a first flow path; a second port enabling liquid communication of the chamber with one or more reservoirs, via a second flow path; a third port enabling gas and liquid communication of the chamber with both one or more receiving containers and a vacuum generator, via a third flow path; and a filter located between the third port and both the first and second port, so that a fluid entering the chamber through the first and/or second
(Continued)

port and exiting the chamber through the third port flows through the filter. The invention also relates to a method using the microfluidic device.

20 Claims, 13 Drawing Sheets

(52) U.S. Cl.
CPC ... *B01L 3/502738* (2013.01); *B01L 3/502753* (2013.01); *B01L 2200/0621* (2013.01); *B01L 2200/0631* (2013.01); *B01L 2200/10* (2013.01); *B01L 2200/146* (2013.01); *B01L 2300/0663* (2013.01); *B01L 2300/0681* (2013.01); *B01L 2300/0861* (2013.01); *B01L 2300/14* (2013.01); *B01L 2400/049* (2013.01); *B01L 2400/0622* (2013.01)

(58) Field of Classification Search
USPC .................................. 436/94; 422/400, 401
See application file for complete search history.

(56) References Cited

U.S. PATENT DOCUMENTS

| | | | |
|---|---|---|---|
| 5,380,437 A * | 1/1995 | Bertoncini | B01D 29/05 210/416.1 |
| 8,747,669 B1 | 6/2014 | Bonner et al. | |
| 2012/0107799 A1* | 5/2012 | Daum | C12Q 1/6806 435/6.1 |
| 2012/0178179 A1* | 7/2012 | Kim | B01L 3/50273 436/180 |
| 2013/0053255 A1 | 2/2013 | Vangbo et al. | |
| 2013/0086998 A1 | 4/2013 | Lee et al. | |
| 2013/0288234 A1 | 10/2013 | Harris et al. | |

OTHER PUBLICATIONS

International Preliminary Report on Patentability directed to related International Patent Application No. PCT/EP2015/070045, dated Mar. 7, 2017; 7 pages.

Shuyi, et al., Medical Microbiology (Second Edition), Beijing Medical University, China Union Medical University, United Press, Feb. 1999; pp. 58-62.

Persing, et al., Molecular Microbiology: Principles and Practices of Diagnostics, Zhongshan University Press, Aug. 2008; pp. 113-120.

Office Action directed to related Chinese Patent Application No. 201580054835.8, dated Nov. 6, 2018, with attached English-language translation; 19 pages.

* cited by examiner

STEP 1   STEP 2

NUCLEIC ACID PURIFICATION CARTRIDGE

INTRODUCTION

The original nucleic acid purification method based on the affinity of DNA and RNA for the silica surfaces (solid phase adsorption) was described by Boom et al. Nucleic acid attraction for silica surfaces is promoted by a high concentration of chaotropic salts (typically guanidine isothiocyanate or guanidine hydrochloride). The Boom method uses a chaotropic salt solution to denaturalize the biological sample and make it go through the filter using centrifugal forces to promote DNA and RNA adsorption onto the silica surface. Once the nucleic acids are bound to the filter, one or more washes with ethanolic buffers are performed to get rid of the chaotropic salts and other biological impurities while keeping nucleic acids bound (chaotropic salts are disruptive for most nucleic acids in downstream applications). As a final step, after getting rid of ethanol (with a high speed spin), nucleic acids need to get rehydrated using an elution buffer (water or low salt buffer). Rehydration promotes unbinding of the DNA and RNA from the silica surface and a final spin yields a solution where purified nucleic acids are resuspended.

Variations of this protocol have been described elsewhere, using either centrifugal force or vacuum as a liquid flow driving force. However, all these methods are rather cumbersome and time-consuming, comprising several pipetting steps and the sequential application of different driving forces to control the flow of liquid, which usually produces a high variation of yield among repeated purification processes.

For example, in a manual execution of the purification protocol by vacuum, the purification process consists of 5 main steps corresponding to the flow of 5 different liquids through the silica filter, i.e.: sample mixture containing the nucleic acids, wash buffer 1 and wash buffer 2 to rinse the filter and eliminate any amounts of contaminants, air to dry out the filter and eliminate any traces of volatile contaminants, and elution buffer to release the nucleic acids from the filter, so that the NAs are further available for downstream applications (such as qPCR amplification and detection). At the end of each step, the vacuum suction is maintained for one or two minutes even after the volume of liquid has flown through the filter. In order to ensure that almost no liquid is left within the filter crevices before the next liquid is pipetted.

The reproducibility of the yield of nucleic acids is dependent on the possibility to reproduce the contact time of the sample and buffers with the filter and the magnitude and distribution of liquid flow, which is dependent on the operator's skill.

It is therefore an object of the invention to provide a purification device which provides reproducible purification results independent of the individual operator.

This is achieved by a microfluidic device and a method for purifying biological or chemical analytes from a complex biological sample. The microfluidic device comprises a chamber wherein a filter is embedded, several reservoirs and valves. The device can be interfaced with external pumps that are operated by an automated instrument. The device and method herein thus provide an end-to-end automated implementation of the classical nucleic acid purification method.

DESCRIPTION

The present invention relates to a microfluidic device having an enclosed chamber containing a filter for purifying biological or chemical analytes from a complex biological sample, said chamber housing a plurality of ports in addition to said filter, as follows: a first port enabling gas communication of the chamber with a vacuum generator, via a first flow path; a second port enabling liquid communication of the chamber with one or more reservoirs, via a second flow path; a third port enabling gas and liquid communication of the chamber with both one or more receiving containers and a vacuum generator, via a third flow path; and a filter located between the third port and both the first and second port, so that a fluid entering the chamber through the first and/or second port and exiting the chamber through the third port flows through the filter.

The herein disclosed invention also relates to a method of purifying a biological or chemical analyte from a complex biological sample using the herein disclosed microfluidic device, the method comprising the steps of: (a) allowing a liquid sample to enter the chamber through the second port by applying a negative pressure difference between the chamber and the first reservoir, while the valves within the flow paths are open for the first and second ports and closed for the third port; (b) allowing the sample to flow through the filter into a first receiving container by applying a negative pressure difference between said first receiving container and the chamber, while the valves within the flow paths are closed for the first port, vented to atmospheric pressure for the second port and open for the third port; and (c) eluting the analyte from the filter by applying a negative pressure difference between the chamber and one of the receiving containers, while the valves within the flow paths are open for the first and second ports and closed for the third port.

DETAILED DESCRIPTION

Purification can in principle be based on any effect widely known in chromatography (e.g. displacement, affinity, cation exchange, anion exchange, size exclusion, reversed phase and normal phase) and its choice mainly depends on the analyte to be purified. Size exclusion is, however, less preferred than the other techniques, because a permanent binding cannot be achieved in the case of the first technique. For the latter one may find conditions, under which the analyte to be purified is selectively bound to the medium, while ideally the other constituents of the sample pass through the medium without binding.

The microfluidic device of the present invention comprises an enclosed chamber containing a filter. A filter herein denotes a medium which differentially interacts with different constituents of a sample. In conventional chromatography such medium would usually be called a stationary phase. The differential interaction (also called partitioning) will cause differential retention times and thus a purification effect, if a sample is moved in a suitable buffer (in chromatography usually called mobile phase) through said medium.

The filter used in the herein disclosed device is one which is suited for purifying biological or chemical analytes from a complex biological sample. The analyte is the substance to be purified. A complex biological sample is a sample which comprises besides the analyte to the purified many different constituents of varying size and chemistry, such as proteins, nucleic acids, hormones, lipids, salts. A preferred sample is a cell lysate.

In a preferred embodiment the filter is made of or at least comprises silica. For example, the filter may be in the form of a silica membrane or a resin containing either silica beads or silica coated beads. Silica surfaces are useful for separating or purifying nucleic acids, in particular DNA. Silica is known to adsorb DNA molecules under certain salt and pH conditions and silica adsorption has become an important technique for purifying DNA.

In one embodiment of the invention the filter element is integrated in the purification cavity and fixated by a fixation ring. In a preferred embodiment the purification membrane filters are inserted in a cavity, which is part of the body of the microfluidic device, and the membrane filter is held in position by a fixation ring that compresses it (FIGS. 2A and 2B).

In an alternative embodiment the purification cavity is a separate part which is assembled into the microfluidic device and eliminates the need for a fixation ring to keep the membrane filter in place. The purification cavity itself provides a clipping feature that fixes the cavity and the membrane filter in position, with the right compression of the membrane (FIGS. 2C and 2D).

A separate cavity, which is hold in position, preferably by a clipping feature, has several advantages compared with cavities comprising a fixation ring:

A reproducible compression of the membrane filter is achieved by a clipping feature. This guarantees a reproducible compression, which generates a reproducible flow of liquids through the membrane filter and therefore a reproducible yield of purified nucleic acids or other purified analyte.

The correct positioning of the purification cavity into the microfluidic device is preferably guaranteed by its clipping feature, without needs to control the amount of compression, which is given by design. This facilitates manufacturing.

The purification cavity eliminates the need for a fixation ring, which results in reduced contamination of the sample. Fixation rings disrupt the fluidic path and gather remnants of liquids, which creates a contamination between buffers and results in a certain amount of contaminants in the final purified eluate, which can inhibit downstream analysis such as PCR. A detachable purification cavity creates a smooth transition on its walls which reduces the amount of contaminants that can be stuck to the wall, typically 5 to 10-fold.

It is preferred that the analytes are nucleic acids. The term nucleic acid comprises mRNA (messenger RNA) in processed and unprocessed form, tRNA (transfer RNA), hnRNA (heterogeneous nuclear RNA), rRNA (ribosomal RNA), LNA (locked nucleic acid), mtRNA (mitochondrial RNA), nRNA (nuclear RNA), siRNA (short interfering RNA), snRNA (small nuclear RNA), snoRNA (small nucleolar RNA), scaRNA (Small Cajal Body specific RNA), microRNA, dsRNA (doubled-stranded RNA), ribozyme, riboswitch, viral RNA, dsDNA (double-stranded DNA), ssDNA (single-stranded DNA), plasmid DNA, cosmid DNA, chromosomal DNA, viral DNA, mtDNA (mitochondrial DNA), nDNA (nuclear DNA), snDNA (small nuclear DNA) or the like or as well as all other conceivable nucleic acids.

The chamber houses a plurality of ports in addition to said filter, as follows: a first port enabling gas communication of the chamber with a vacuum generator, via a first flow path; a second port enabling liquid communication of the chamber with one or more reservoirs, via a second flow path; a third port enabling gas and liquid communication of the chamber with both one or more receiving containers and a vacuum generator, via a third flow path.

The vacuum generator is located upstream of the chamber. The one or more reservoirs are also located upstream of the chamber, but in another flow path than the vacuum generator. The one or more receiving containers are located downstream of the chamber. Further downstream of the receiving container(s) the vacuum generator of the third flow path is located.

The reservoir(s) usually comprise at least a reservoir containing the sample to be purified and optionally one or more reservoirs comprising one or more washing buffers and/or an elution buffer and/or a regeneration buffer. The one or more containers usually comprise at least one container for receiving the analyte and optionally one or more containers for receiving other liquids, e.g. the flow through, washing buffer(s) and/or regeneration buffer(s).

A filter is located between the third port and both the first and second port, so that a fluid entering the chamber through the first and/or second port and exiting the chamber through the third port flows through the filter. Most conveniently the filter expands across the complete cross-section of the chamber. It is, however, not necessary that the medium fill up the full height of the chamber. Preferably, the filter is placed directly over the third port.

It is preferred that the device is a microfluidic cartridge. A cartridge means a consumable component which can be actuated by a larger unit through a suitable interface. Usually, the unit contains costly and/or endurable elements or elements which are easy to clean, and a piece of software code to automate the control of the process. The unit may alternatively comprise further elements for performing other processes upstream or downstream of the purification unit.

In one embodiment the device is disposable meaning that the device is designed for a single use after which it is disposed. In another embodiment the device is reusable which usually necessitates a regeneration of the device after each use.

The device may further comprise the valves ideally the vacuum generator is separate. The vacuum generator evacuates the chamber's pressure thereby generating a relative negative pressure. Depending on the ports configuration (i.e. open or closed), a fluid is sucked from one of the reservoirs into the chamber and/or out of the chamber into one of the receiving containers. In a preferred embodiment the vacuum generator is a syringe pump or a diaphragm pump. In a further preferred embodiment, the vacuum can be applied to the first port and/or the third port with the same vacuum generator.

Known microfluidic devices do not include means for tracking the pressure in the system. The present invention preferably includes one or more pressure sensors. A Pressure sensor is preferably located within the third flow path upstream of the receiving containers. Another pressure sensor is preferably located within the first flow path downstream of the vacuum generator. The above pressure sensors may be used to determine the pressure drop caused by the filter which indicates the fluidic state of the filter. Thereby, one may determine (i) when a method step is completed thus minimizing time and buffers (e.g. when the filter is completely dry during a drying step; when the filter is sufficiently purged of liquid leftovers during the purging steps, which advantageously take place after the flow of each liquid and before the flow of the next one); (ii) if the liquids have flown completely through the filter, allowing the system to apply a 'just-in-time' increase in the suction pressure if there is an increased resistance to liquid flow due to the density and viscosity of the sample; (iii) if the filter is clogged; and (iv) the time required for each liquid to flow through the filter, which can be compared to a pre-determined threshold as a control for the purification method.

As described above, the herein disclosed device has three ports for communication with the chamber: a first port (gas outlet port), a second port (liquid inlet port) and a third port (liquid/gas outlet port). Each port can be individually opened, closed or vented to the atmosphere by means of a valve located within the respective flow path. Conveniently, multiport valves are used and, if desired, two or three ports actuated with the same multiport valve. It is preferred that the dead volume enclosed by the third flow path between its corresponding valve and the filter is between 1 uL and 10 mL. The controlled flow of liquids (including no-flow situation for a complete wetting of the filter) is achieved by applying a vacuum to the appropriate port and by opening and closing the appropriate valves at each step. This confers a higher reproducibility to the device than the known devices independently of the biological sample type.

For example, in a conventional purification kit with a manual execution of the purification protocol by vacuum, the purification process consists of five main steps corresponding to the flow of five different liquids through the filter, i.e. loading a sample mixture containing the nucleic acids, washing with wash buffer 1 and wash buffer 2 to rinse the filter and eliminate any amounts of contaminants, air drying the filter and eliminating any traces of volatile contaminants, and eluting to release the nucleic acids from the filter in order to be further available for downstream applications (such as qPC amplification and detection). At the end of each step, the vacuum suction is maintained for one or two minutes even after the volume of liquid has flown through the filter in order to ensure that almost no liquid is left within the filter crevices before the next liquid is pipetted, an operation that is referred to as 'purging'.

In order to achieve the same effect, the automated protocol comprises basically the same steps, which are achieved by connecting each port to the appropriate reservoirs and applying the appropriate pressure differences at all times, by means of a pressure source (e.g. syringe or rotary pump), a set of valves, a set of microfluidic channels and a microcontroller using a software to automate all the steps.

The herein disclosed microfluidic device is particularly suited for being used in methods in which one or more analytes are to be separated from other constituents, i.e. in a purification method. Therefore, another object of the invention is a method of purifying a biological or chemical analyte from a complex biological sample using the microfluidic device described herein, the method comprising in this order the following steps: (a) allowing a liquid sample to enter the chamber through the second port by applying a negative pressure difference between the chamber and the first reservoir, while the valves within the flow paths are open for the first and second ports and closed for the third port; (b) allowing the sample to flow through the filter into a first receiving container by applying a negative pressure difference between said first receiving container and the chamber, while the valves within the flow paths are closed for the first port, vented to atmospheric pressure for the second port and open for the third port; and (c) eluting the analyte from the filter by applying a negative pressure difference between the chamber and one of the receiving containers, while the valves within the flow paths are open for the first and second ports and closed for the third port.

The pressure in step a may be generated by the vacuum generator located in the first flow path. The pressure in step b may be generated by the vacuum generator located in the third flow path.

The elution in step c may be carried out in detail as follows:

i) allowing an elution buffer contained in a third reservoir to enter the chamber through the second port by applying a negative pressure difference between the chamber and the third reservoir, while the valves within the flow paths are open for the first and second ports and closed for the third port. The pressure may be generated by the vacuum generator located in the first flow path; and ii) allowing the elution buffer to be in contact with the filter for a predetermined time, while the valves within the flow paths are open for the first and second ports and closed for the third port. This step allows sufficient wetting of the filter in order to release the desired analyte; and iii) allowing the elution buffer (containing the released analyte) to flow through the filter into a second receiving container by applying a negative pressure difference between said second receiving container and the chamber, while the valves within the flow paths are closed for the first port, vented to atmospheric pressure for the second port and open for the third port. The pressure may be generated by the vacuum generator of the third flow path.

Preferably, the method further comprises between steps a and b the step of allowing the sample to be in contact with the filter for a predetermined time, while the valves within the flow paths remain open for the first and second ports and closed for the third port.

The method may optionally comprise between steps b and c one or more of the following steps:

(i) cleaning and drying the filter for a predetermined time by applying a negative pressure between the third flow path and the chamber, said negative pressure difference being generated by the vacuum generator located in the third flow path, while the valves within the flow paths are closed for the first port, vented to atmospheric pressure for the second port and open for the third port; and/or (ii) allowing a washing buffer located in a second reservoir to enter the chamber through the second port and to flow through the filter and into a receiving container by applying a negative pressure difference between said receiving reservoir and said second reservoir, while the valves within the fluidic paths are open for the second and third ports and closed for the first port. The pressure may be generated by the vacuum generator located in the third flow path; and/or iii) allowing gas to flow through the filter for a predetermined time, by applying a negative pressure between the third flow path and the chamber, while the valves within the flow paths are closed for the first port, vented to atmospheric pressure for the second port and open for the third port. The gas displaces liquid and dries the filter. The pressure may be generated by the vacuum generator located in the third flow path.

Preferably, the pressure difference is determined in order to determine when one or more valves are to be switched and, thus, the next method step is to be performed. A pressure drop across the filter indicates that valve(s) can be actuated to perform the next method step.

It is further preferred that the gas flow for drying the filter is applied only if the value of the first derivative of the pressure difference between the first and second pressure sensors is below a predefined threshold value.

Table 1 details one example of the method steps to be performed for a purification process by automatic means. Fluidic diagrams shown in the figures show the port/valve configuration for each of said steps.

TABLE 1

Detailed protocol for an example of a purification process.

| | | | |
|---|---|---|---|
| SAMPLE | Step 1 | FIG. 3 | Initial step__Sample to purification filter |
| | Step 2 | FIG. 4 | Sample to purification filter (plunger drive) |
| | Step 3 | FIG. 5 | Pressure release |
| | Step 4 | FIG. 6 | Plunger to home |

TABLE 1-continued

Detailed protocol for an example of a purification process.

|  | Step 5 | FIG. 7 | Incubation of Sample |
|---|---|---|---|
|  | Step 6 | FIG. 8 | Sample from purification filter to waste/container n° 13 (plunger drive) |
|  | Step 7 | FIG. 5 | Pressure release |
|  | Step 8 | FIG. 6 | Plunger to home |
|  | Step 9 | FIG. 9 | Purge |
| WASH 1 | Step 10 | FIG. 3 | Wash 1 to purification filter |
| (valve n° 7-> position 2; | Step 11 | FIG. 4 | Wash 1 to purification filter (plunger drive) |
| Reservoir n° 16) | Step 12 | FIG. 5 | Pressure release |
|  | Step 13 | FIG. 6 | Plunger to home |
|  | Step 14 | FIG. 7 | Incubation of Wash Buffer 1 |
|  | Step 15 | FIG. 8 | Wash 1 from purification filter to waste/container n° 13 (plunger drive) |
|  | Step 16 | FIG. 5 | Pressure release |
|  | Step 17 | FIG. 6 | Plunger to home |
|  | Step 18 | FIG. 9 | Purge |
| WASH 2 | Step 19 | FIG. 3 | Wash 2 to purification filter |
| (valve n° 7 -> position 3; | Step 20 | FIG. 4 | Wash 2 to purification filter (plunger drive) |
| Reservoir n° 17) | Step 21 | FIG. 5 | Pressure release |
| (plunger drive) | Step 22 | FIG. 6 | Plunger to home |
|  | Step 23 | FIG. 7 | Incubation of Wash Buffer 2 |
|  | Step 24 | FIG. 8 | Wash 2 from purification filter to waste/container n° 13 |
|  | Step 25 | FIG. 5 | Pressure release |
|  | Step 26 | FIG. 6 | Plunger to home |
|  | Step 27 | FIG. 9 | Purge |
| DRYING | Step 28 | FIG. 10 | Drying of the purification filter |
| ELUTION | Step 29 | FIG. 3 | Elution buffer to purification filter |
| (valve n° 7 -> position 4; | Step 30 | FIG. 4 | Elution buffer to purification filter (plunger drive) |
| Reservoir n° 18) | Step 31 | FIG. 5 | Pressure release |
|  | Step 32 | FIG. 6 | Plunger to home |
|  | Step 33 | FIG. 11 | Incubation of Elution Buffer |
| ELUTION | Step 34 | FIG. 12 | Elution buffer from purification filter to container n° 14 (plunger drive) |

The invention has the advantage that whole automation can be achieved and no manual manipulation is needed for the purification process to be completed, thus achieving reproducible results. Further, the purification device/process can be linked to other upstream or downstream devices/processes (e.g., lysis, amplification and detection). In contrast with the prior art, liquids are moved into the chamber and onto the filter by means of a vacuum applied to the first port, while the third port is closed. This prevents flow through the filter while allowing pre-wetting of the filter for a predetermined incubation time. Liquids are moved through the filter by means of a vacuum applied to the third port, after opening the valve of that port. Taken together, equal or higher nucleic acid yields are obtained as compared to known methods.

FIGURE CAPTIONS

Figure 1:
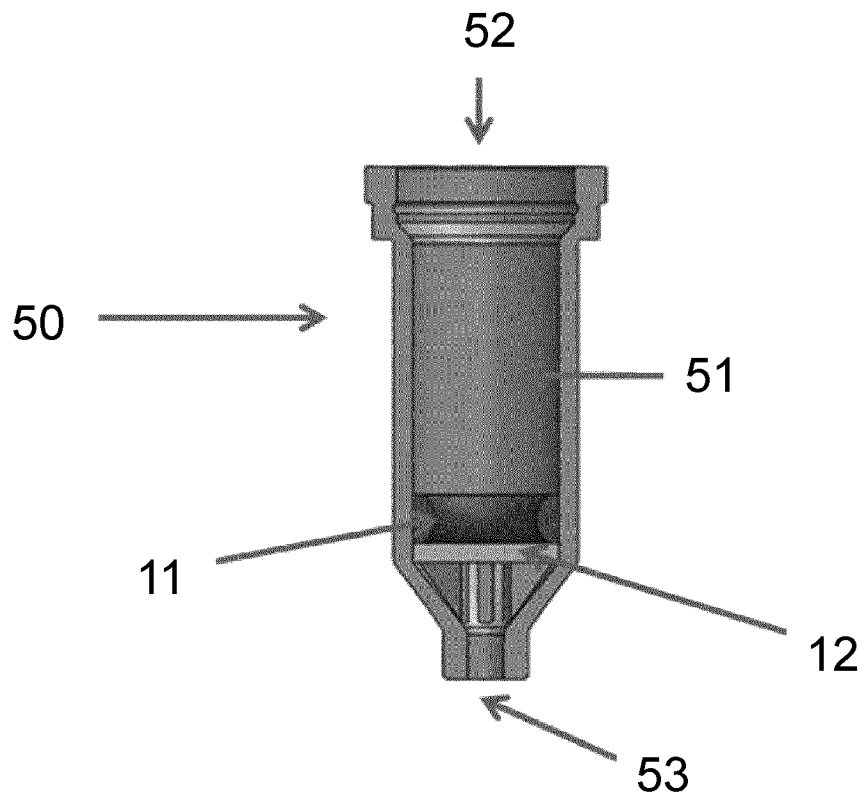
FIG. 1 shows a purification column (50) from a commercial kit for manual purification consisting of a plastic body (51) and a membrane filter (12) compressed and held in place by a fixation ring (11). The plastic body comprises a liquid inlet (52) and a liquid outlet (53).
Figure 2A:
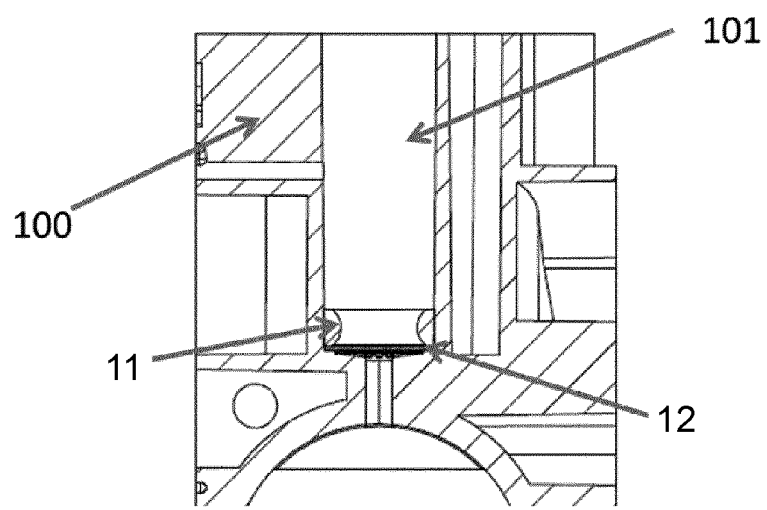
FIG. 2A shows part of a microfluidic device (100) with an integrated purification cavity (101), and a membrane filter (12) held in place by a fixation ring (11).
Figure 2B:
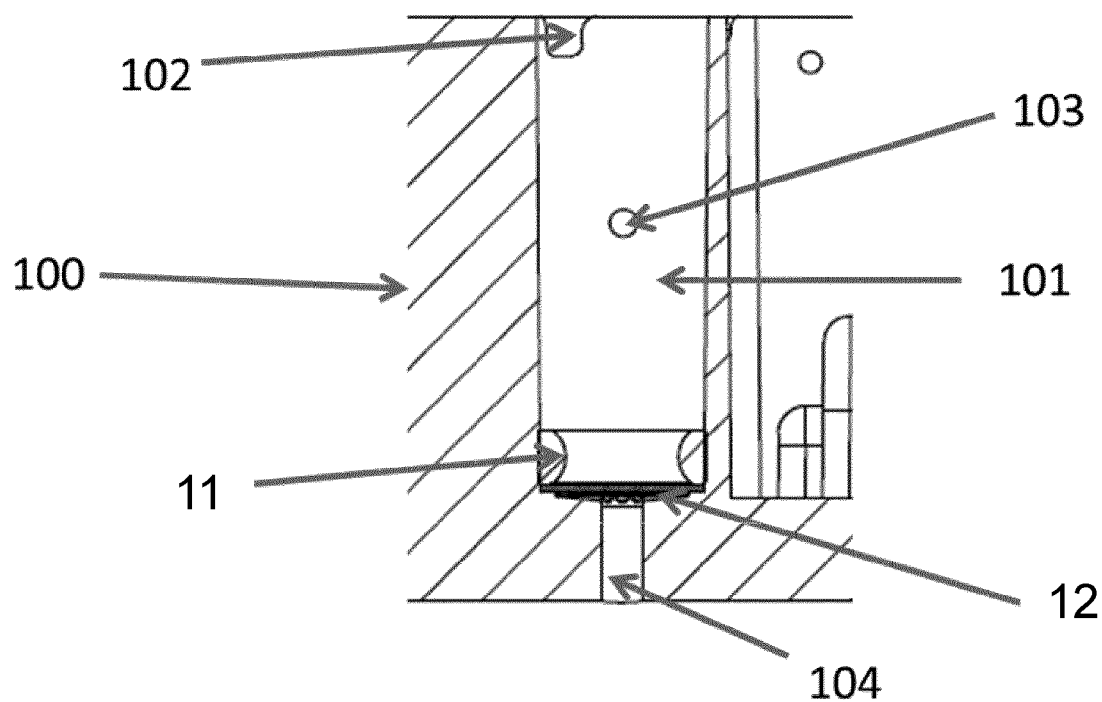
FIG. 2B shows a rotated view for the microfluidic device (100) with an integrated purification cavity (101), and a membrane filter (12) held in place by a fixation ring (11). The gas port (102), liquid inlet port (103) and outlet port (104) connected to the purification cavity (101) are also shown.
Figure 2C:
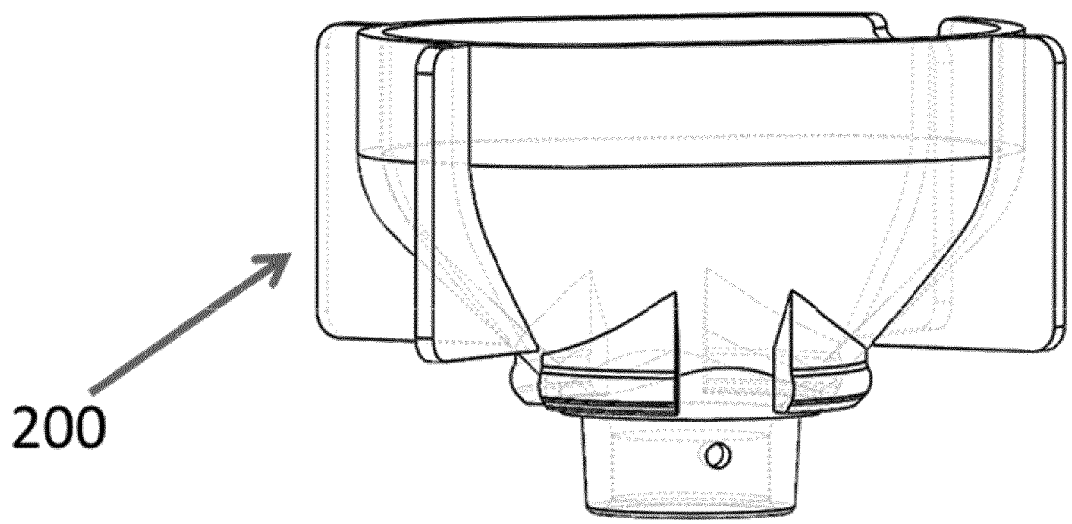
FIG. 2C shows a separate purification cavity (200).
Figure 2D:
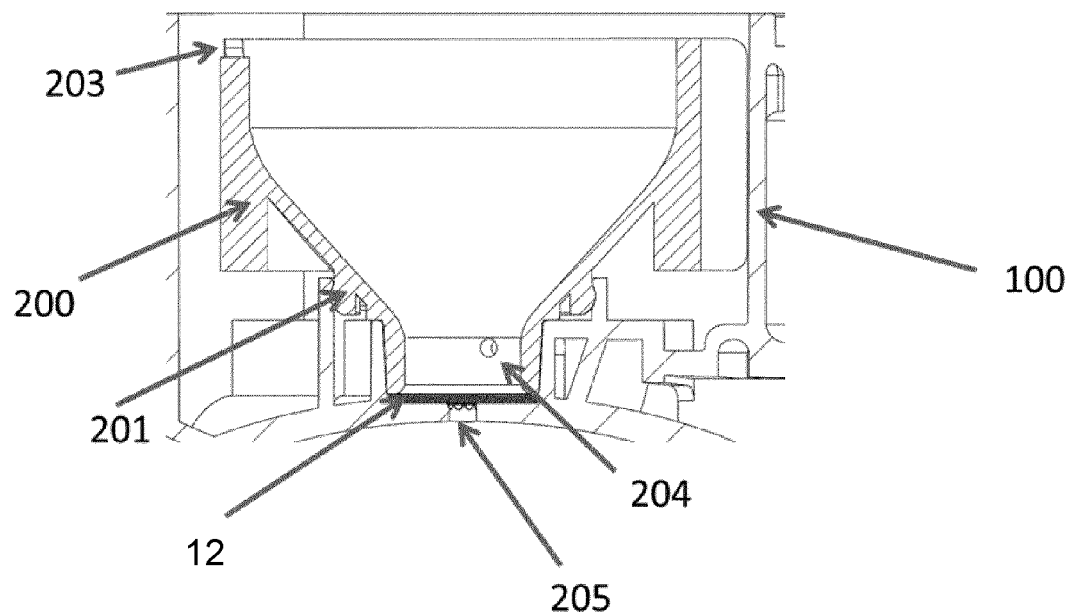

FIG. 2D shows a purification cavity (200) assembled in a microfluidic device (100). The clipping feature (201) holds the purification cavity (200) in place and applies the right compression to the membrane filter (12). The gas port (203), liquid inlet port (204) and outlet port (205) are also shown.

Figure 2E:
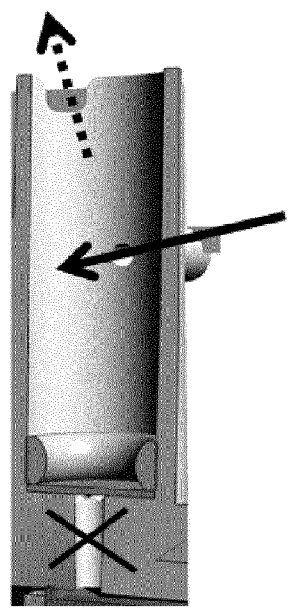
Figure 2E:
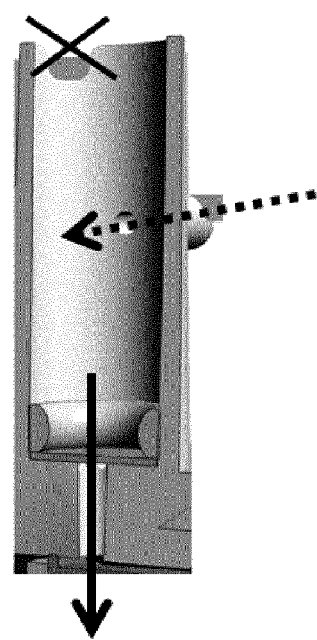
Figure 3:
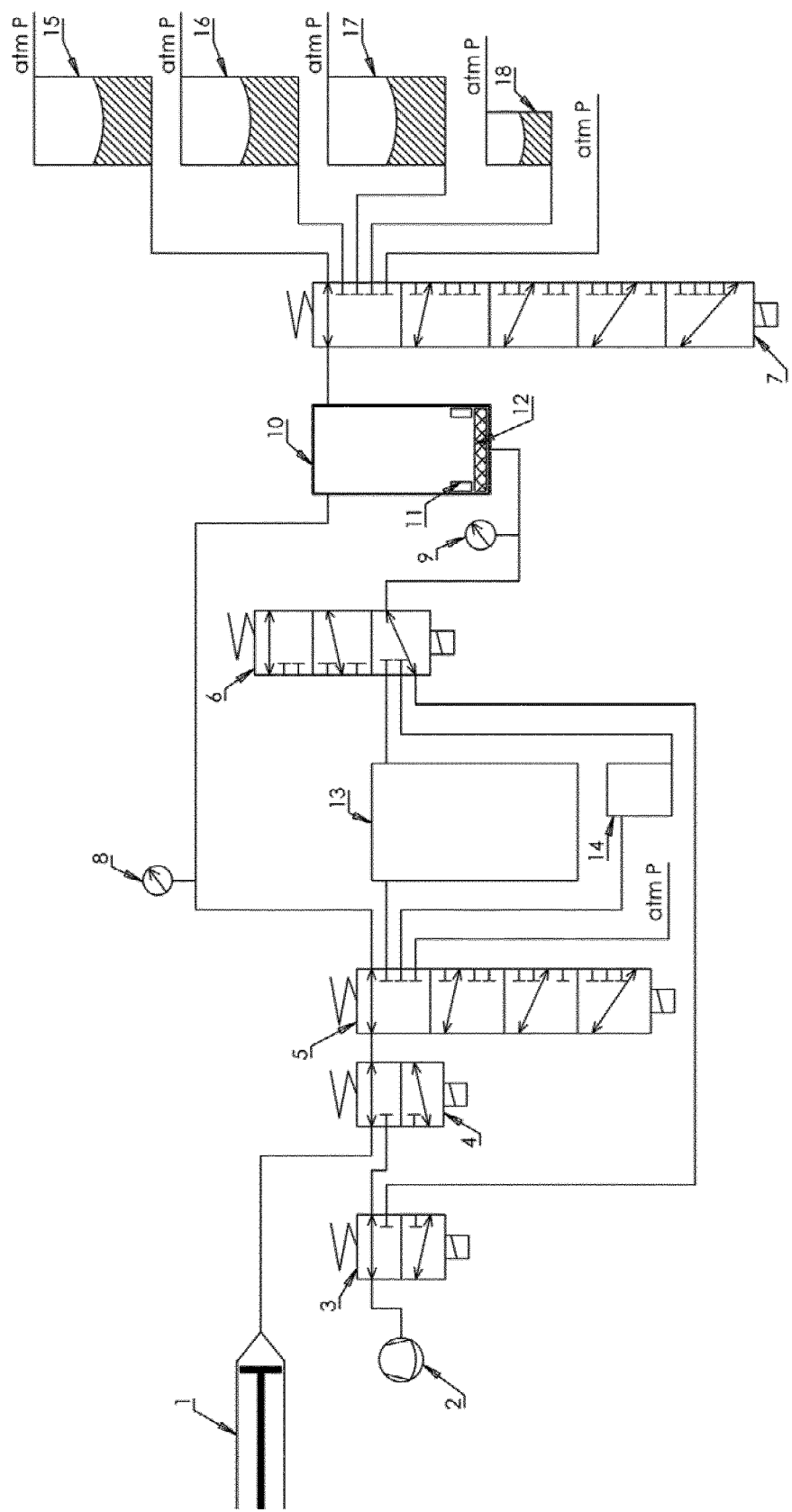
Figure 4:
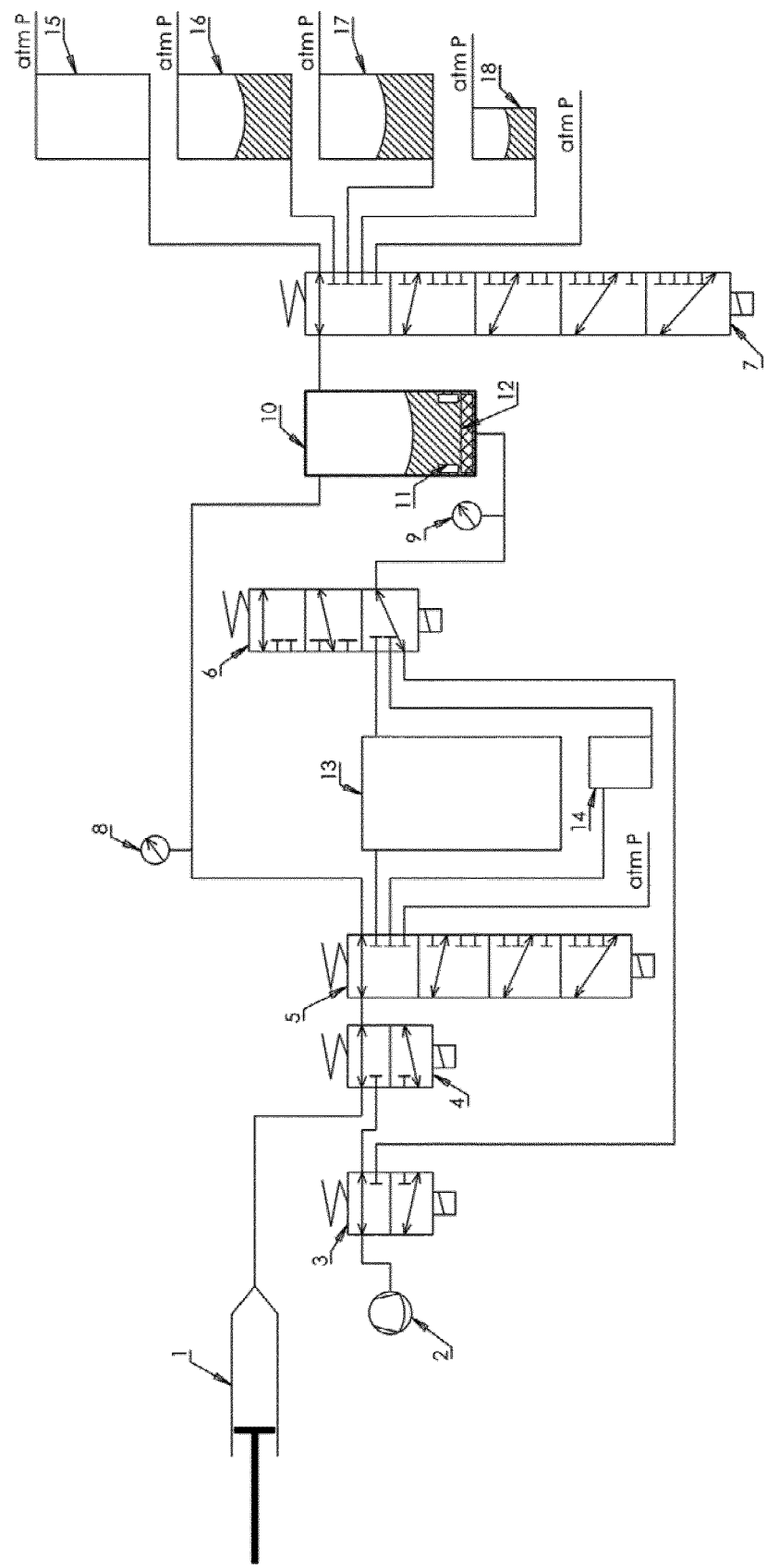
Figure 5:
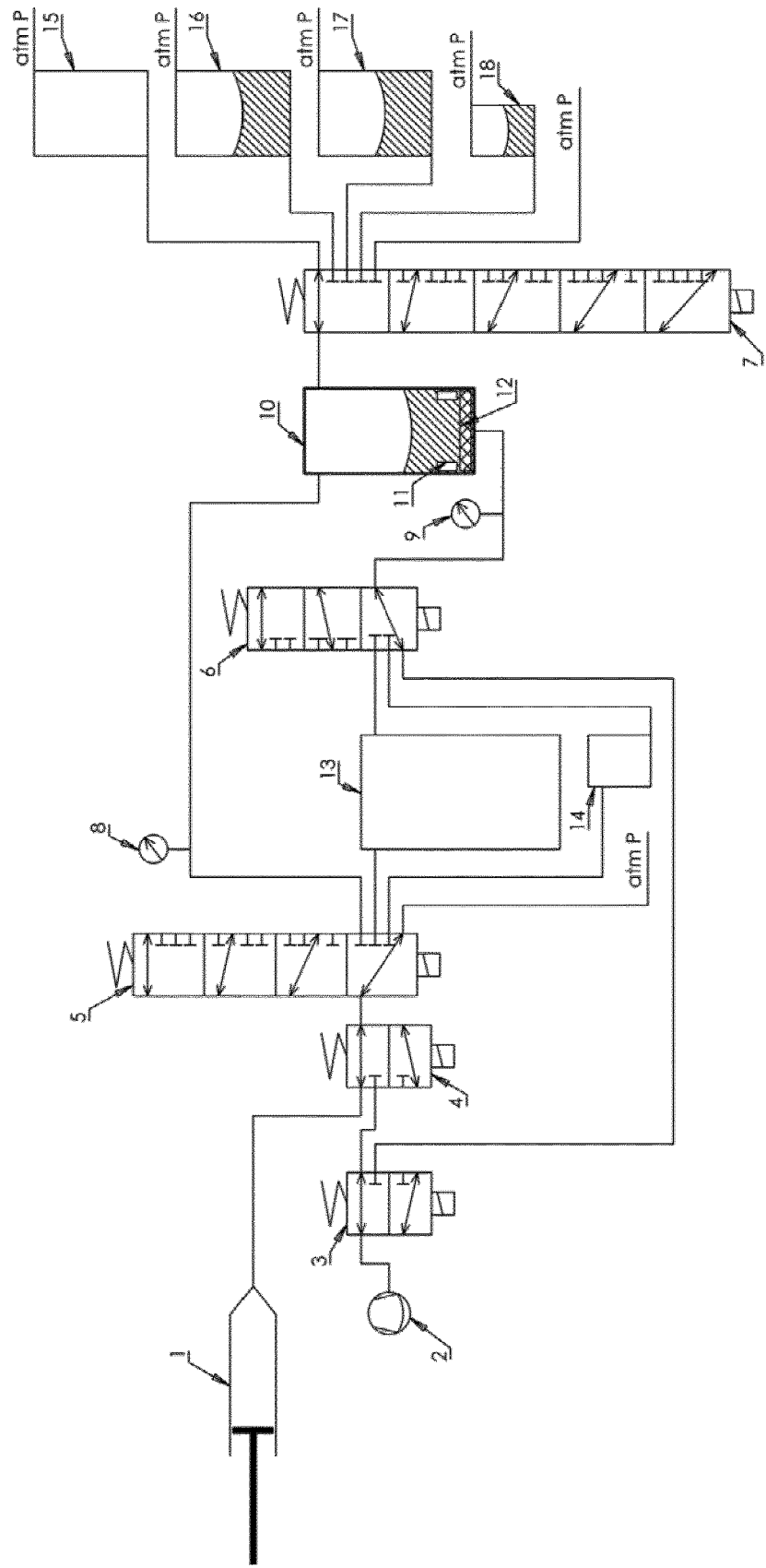
Figure 6:
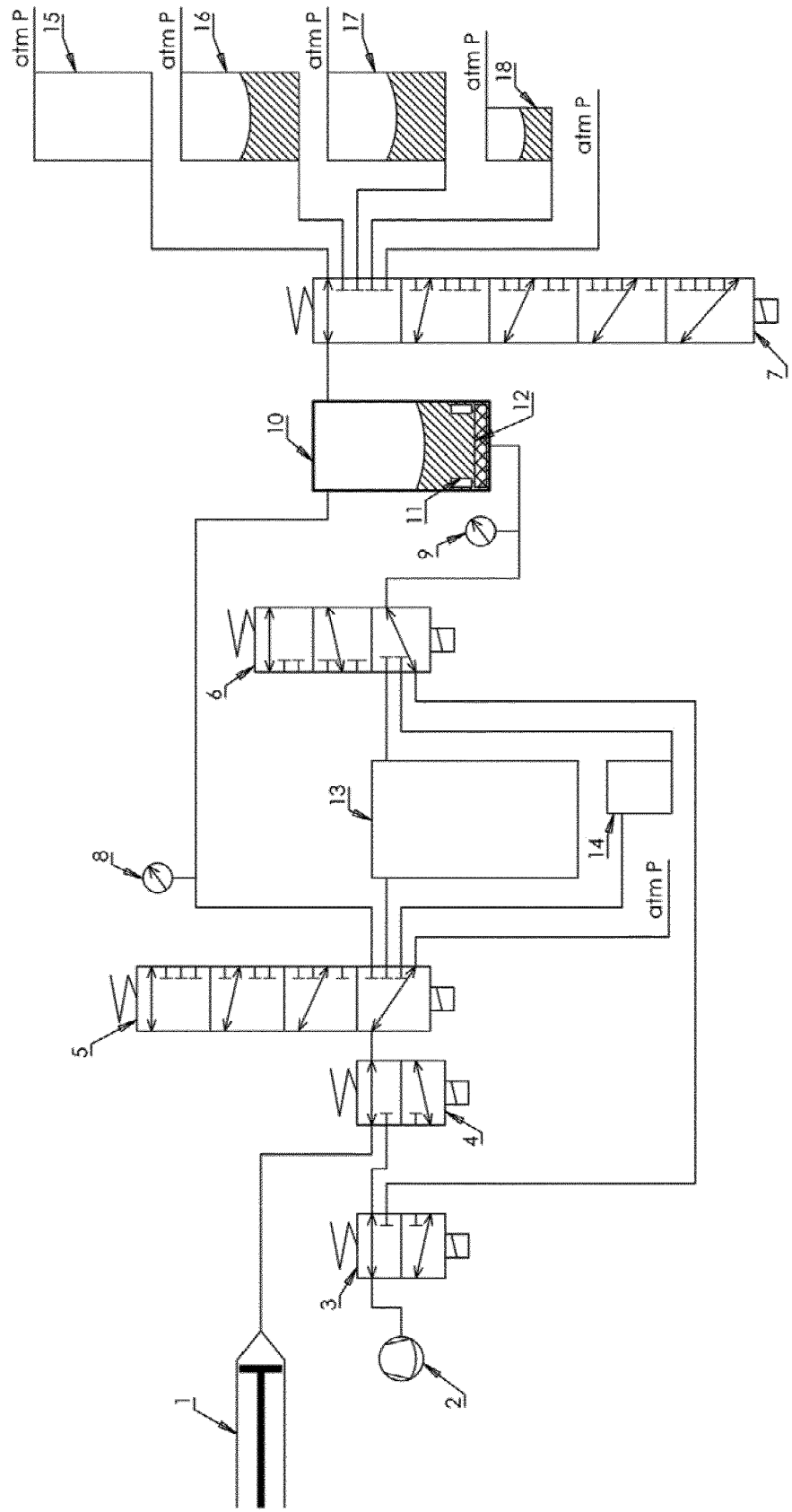
Figure 7:
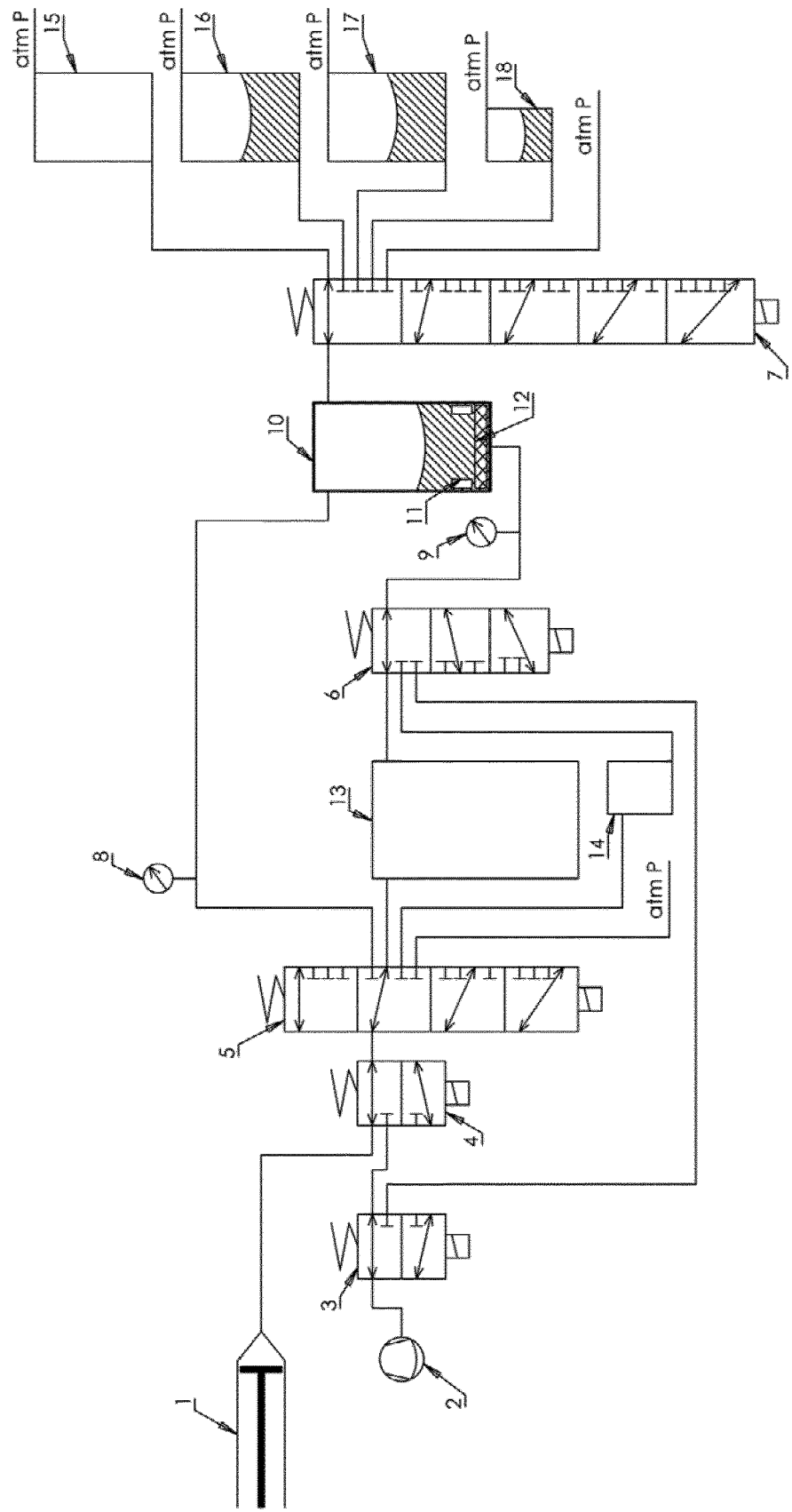
Figure 8:
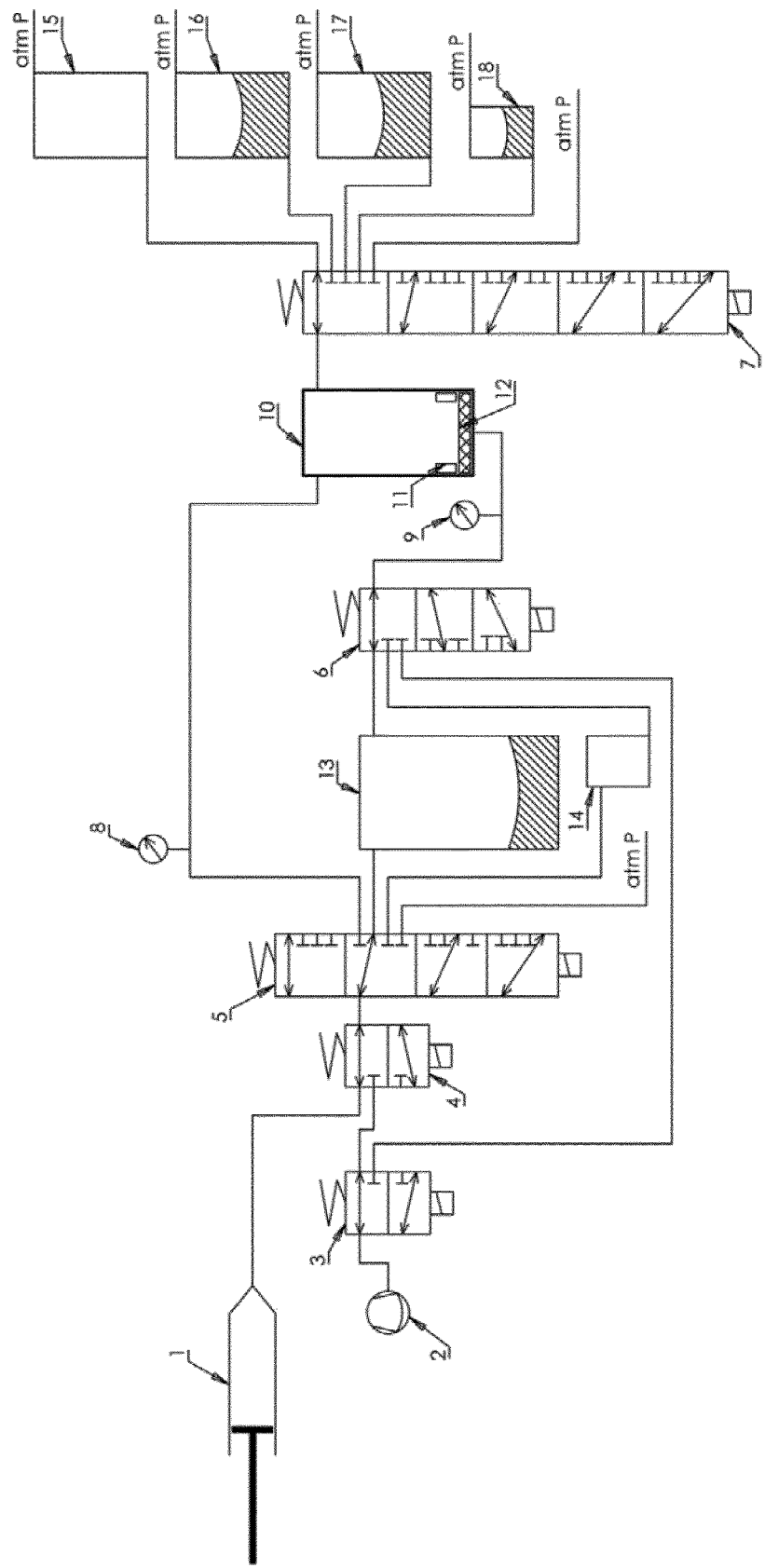
Figure 9:
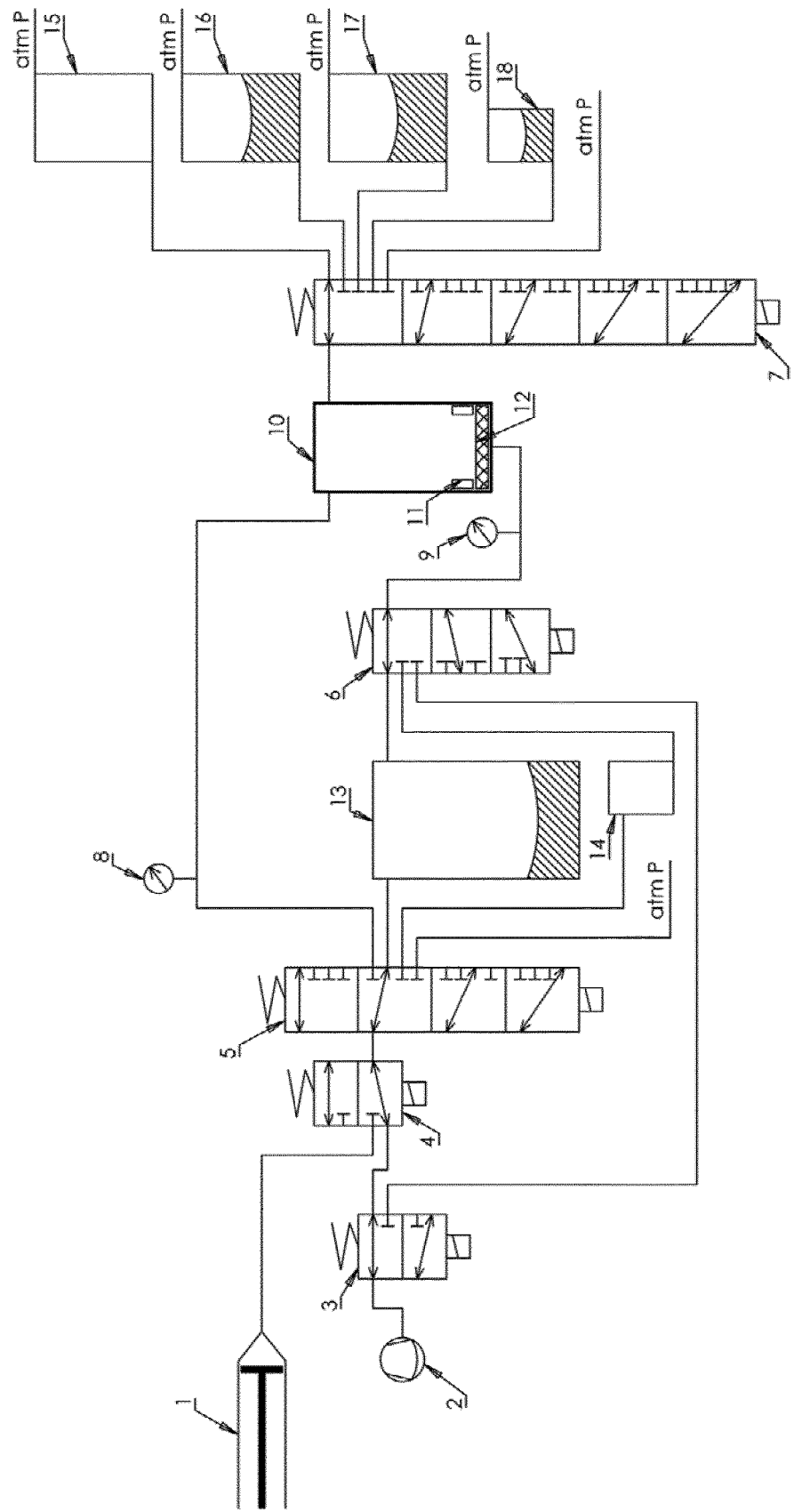
Figure 10:
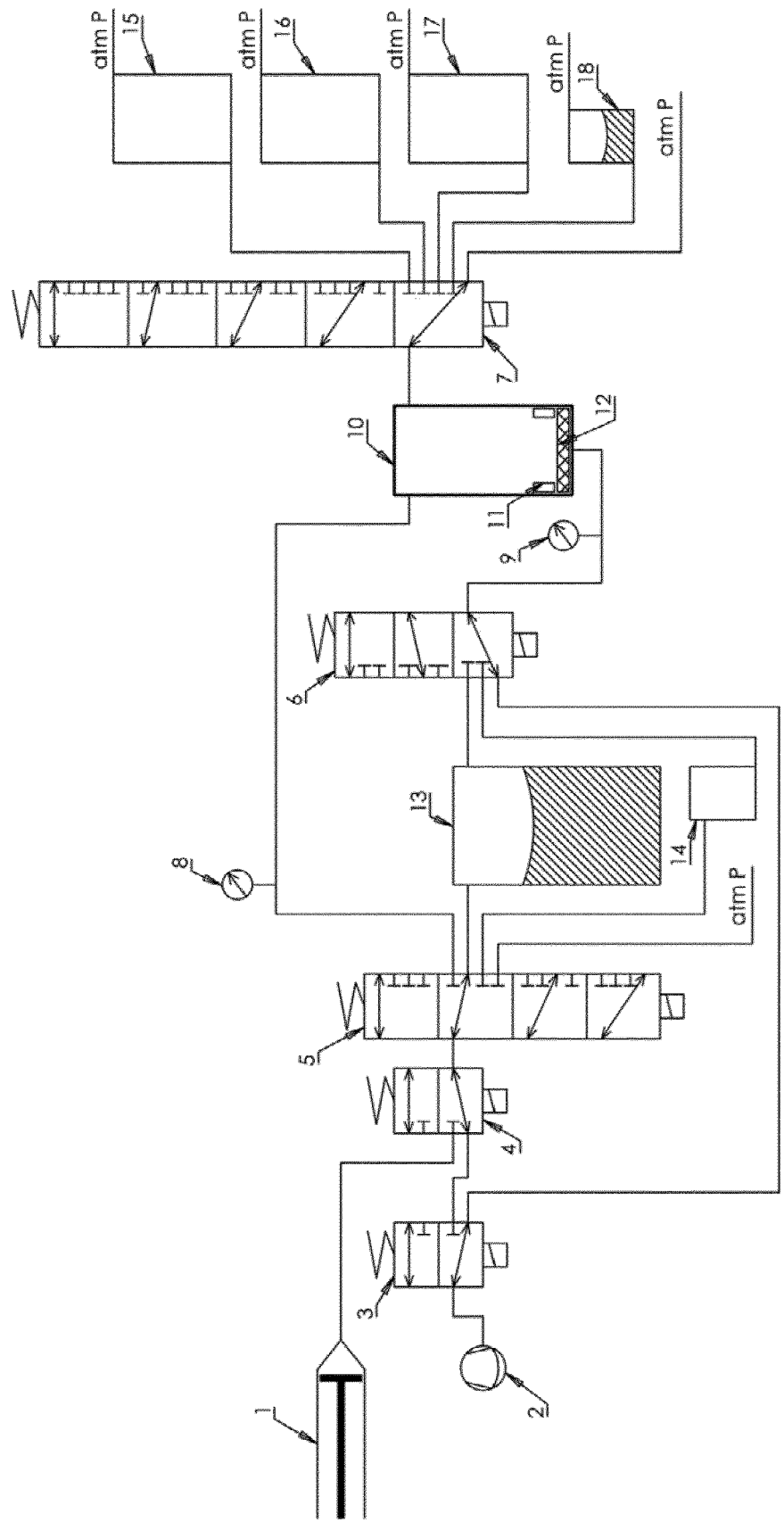
Figure 11:
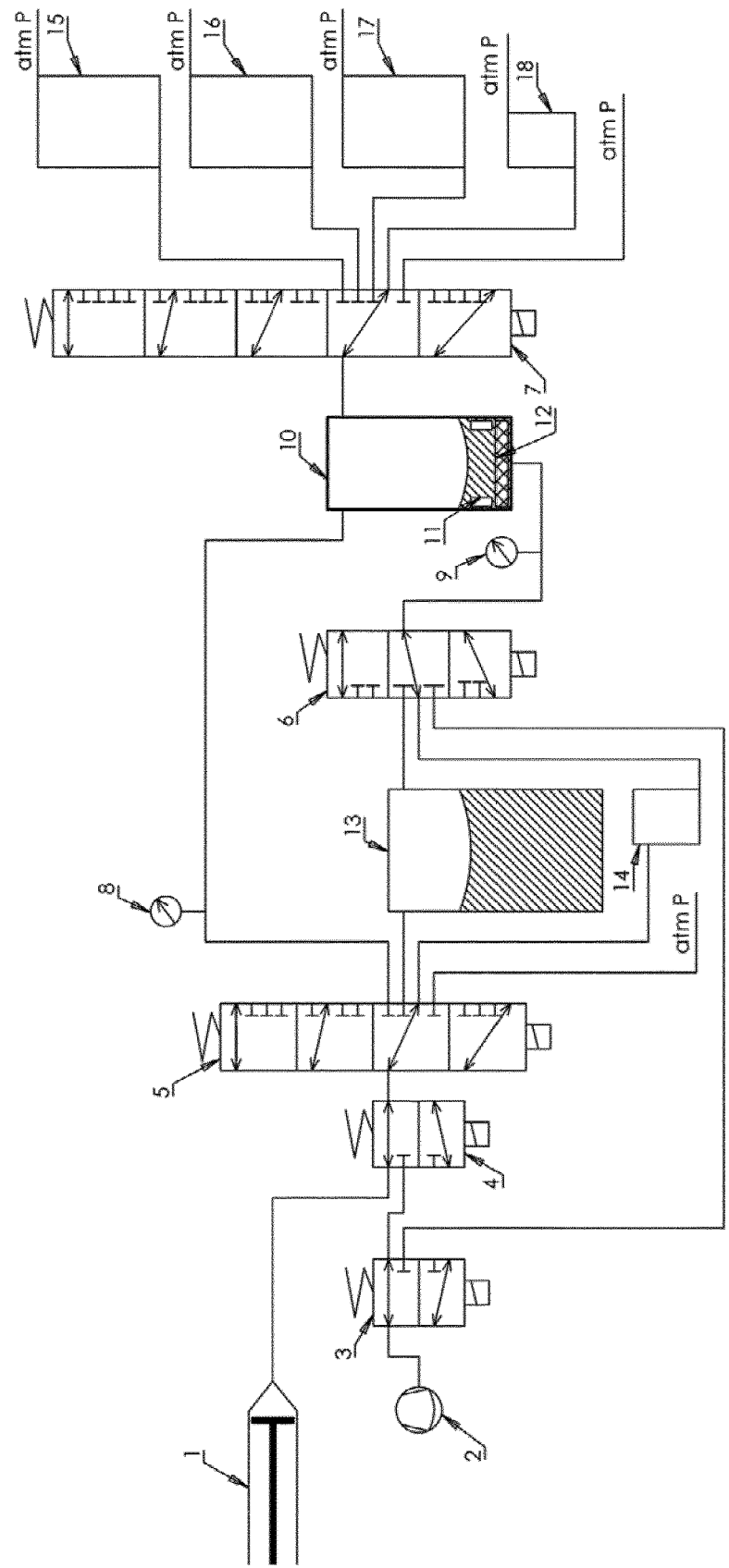
Figure 12:
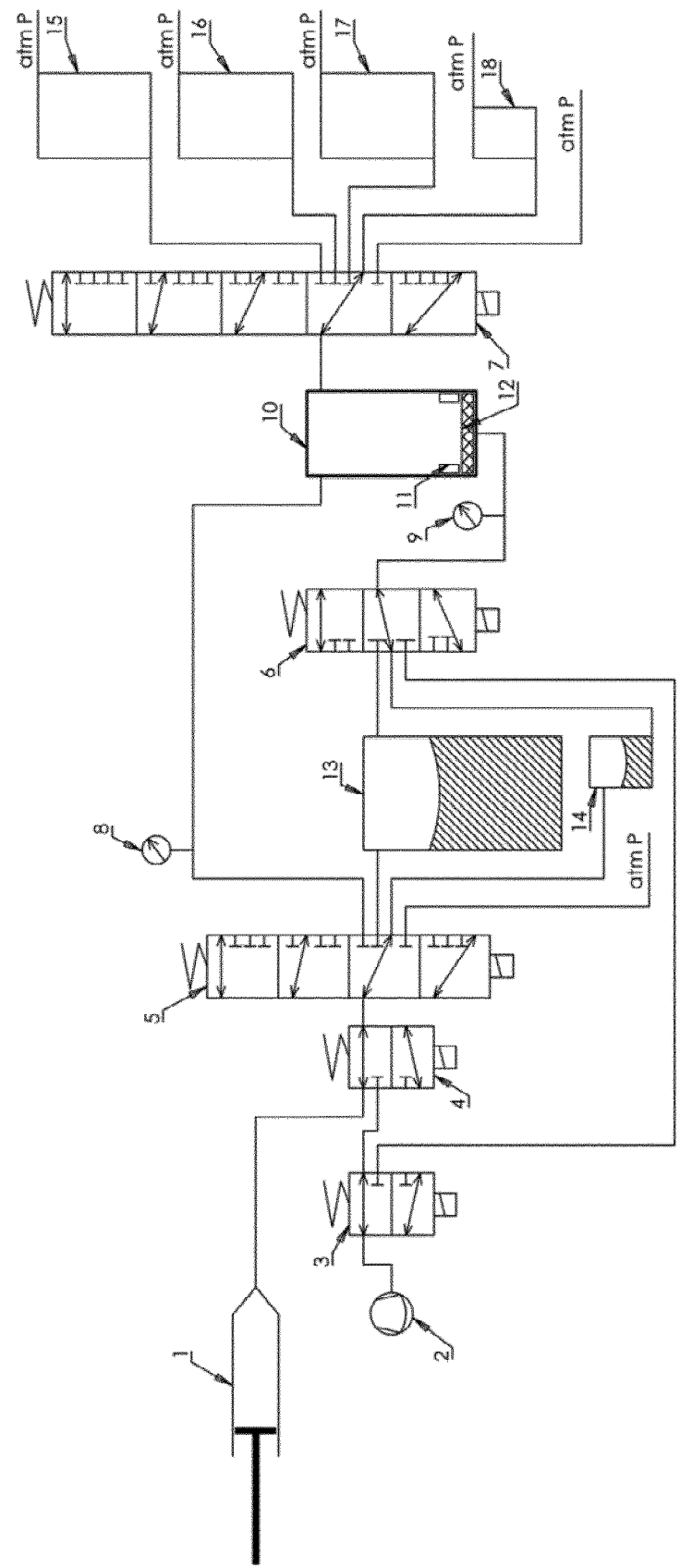

FIG. 2E illustrates the port configuration and the flow direction during loading of liquid (STEP 1) and washing/elution (STEP 2). Solid arrow indicates liquid flow; dotted arrow indicates gas flow; X indicates port closed by valve.

FIGS. 3 to 12: Detailed fluidic diagrams showing the port/valve configuration for each of the steps detailed in table 1. It is to be understood that the device of the present invention may but does not necessarily comprise each of the elements shown in the figures. The description and/or claims denote the essential elements. In addition to said elements one or more further optional elements may be independently chosen from each other. The optional elements are indicated in the following. 1: vacuum generator 1 (e.g. syringe pump); 2: vacuum generator 2 (optional, e.g. diaphragm pump); 3-7: valves (e.g. multiport valves); 8 and 9: pressure sensors (optional); 10: chamber; 11: fixation ring (optional); 12: filter; 13: waste receiving container (optional); 14: eluate receiving container; 15: sample reservoir; 16-17: reservoirs (optional); 18: elution buffer reservoir.

The invention claimed is:

1. A microfluidic device comprising:
   one or more reservoirs upstream of a purification cavity;
   one or more waste receiving containers downstream of the purification cavity;
   the purification cavity defining an enclosed column with a tapered shape and hollow interior configured to be detachable from the microfluidic device, the purification cavity separate from and non-contiguous with any of the reservoirs or receiving containers, and comprising:
   a first port configured to provide gas communication between the purification cavity and a vacuum generator, via a first flow path;
   a second port configured to provide liquid communication between the purification cavity and the one or more reservoirs, via a second flow path; and
   a third port configured to provide gas and liquid communication between the purification cavity and both the one or more waste receiving containers and the vacuum generator, via a third flow path; wherein the first, second, and third ports are positioned on an exterior peripheral surface of the purification cavity, and
   a filter spanning a cross-section of the purification cavity orthogonal to the direction of liquid flow, configured to purify biological or chemical analytes from a complex biological sample and located adjacent to the third port such that fluid entering the purification cavity through the first or second port and exiting the bottom of the purification cavity through the third port flows through the filter.

2. The microfluidic device of claim 1, wherein the microfluidic device is a microfluidic cartridge and is designed to be disposable.

3. The microfluidic device of claim 1, wherein the microfluidic device is a microfluidic cartridge and is reusable.

4. The microfluidic device of claim 1, wherein the biological or chemical analytes comprise nucleic acids.

5. The microfluidic device of claim 1, wherein the filter comprises silica.

6. The microfluidic device of claim 5, wherein the filter comprises a silica membrane.

7. The microfluidic device of claim 5, wherein the filter comprises a resin containing silica beads.

8. The microfluidic device of claim 5, wherein the filter comprises a resin containing silica-coated beads.

9. The microfluidic device of claim 1, wherein the purification cavity comprises a clipping feature configured to fix the position of the purification cavity in the microfluidic device.

10. The microfluidic device of claim 1, wherein the vacuum generator is a syringe pump, a diaphragm pump, or a combination of the two.

11. The microfluidic device of claim 1, further comprising a first pressure sensor located within the third flow path between the purification cavity and the one or more waste receiving containers.

12. The microfluidic device of claim 11, further comprising a second pressure sensor located within the first flow path between the purification cavity and the vacuum generator.

13. The microfluidic device of claim 1, further comprising one or more multiport valves coupled to each of the first flow path, second flow path, and third flow path.

14. The microfluidic device of claim 13, wherein the one or more multiport valves are triggered by a pressure difference.

15. The microfluidic device of claim 13, wherein a dead volume enclosed by the third flow path between one of its corresponding one or more multiport valves and the filter is between 1 µL and 10 mL.

16. A method of purifying a biological or chemical analyte from a complex biological sample using the microfluidic device according to claim 1, the method comprising the steps of:

applying a negative pressure difference between the purification cavity and a first reservoir to flow a liquid sample into the purification cavity through the second port;

applying a negative pressure difference between a first receiving container and the purification cavity to flow the liquid sample through the filter and out the third port; and eluting the biological or chemical analyte from the filter by applying a negative pressure difference between the purification cavity and a second receiving container to flow an elution buffer through the filter and out the third port.

17. The method of claim 16, wherein the eluting further comprises:

applying a negative pressure difference between the purification cavity and a second reservoir to flow the elution buffer into the purification cavity through the second port; and incubating the elution buffer with the filter for a predetermined incubation time.

18. The method of claim 16, further comprising incubating the liquid sample with the filter for a predetermined incubation time.

19. The method of claim 16, further comprising applying a negative pressure between the vacuum generator and the purification cavity via the third port to flow gas through the filter.

20. The method of claim 16, further comprising applying a negative pressure difference between a third reservoir and the first receiving container to flow a washing buffer located in the third reservoir through the second port of the purification cavity and out the third port of the purification cavity.

* * * * *